United States Patent [19]
Sirkar et al.

[11] Patent Number: 6,110,481
[45] Date of Patent: Aug. 29, 2000

[54] CONTROLLED RELEASE DEVICE BASED ON AQUEOUS-ORGANIC PARTITIONING IN POROUS MEMBRANES

[75] Inventors: Kamalesh K. Sirkar, Berkeley Heights; Stephanie Farrell, Bloomfield, both of N.J.; Rahul Basu, Fayetteville, Ark.

[73] Assignee: Trustees of the Stevens Institute of Technology, Hoboken, N.J.

[21] Appl. No.: 08/205,996

[22] Filed: Mar. 4, 1994

[51] Int. Cl.[7] .................................................... A61K 9/70
[52] U.S. Cl. ..................... 424/422; 424/423; 424/424; 424/425; 424/426; 424/443; 424/444; 424/447; 424/448; 424/449
[58] Field of Search ................................... 424/423–426, 424/443–449, DIG. 7; 239/53

[56] References Cited

U.S. PATENT DOCUMENTS

| | | | |
|---|---|---|---|
| 3,625,214 | 12/1971 | Higuchi | 424/424 |
| 3,699,956 | 10/1972 | Kitrilakis et al. | 128/348 |
| 3,796,217 | 3/1974 | Arlen | 128/260 |
| 4,351,337 | 9/1982 | Sidman | 128/260 |
| 5,028,435 | 7/1991 | Katz et al. | |
| 5,292,515 | 3/1994 | Moro et al. | 424/422 |

OTHER PUBLICATIONS

Langer, R., "New Methods of Drug Delivery", *Science*, 249, 1527–1533, 1990.

Vyavahare et al., "Zero Order Release from Glassy Hydrogels. II Matrix Effects", *J. Membrane Sci.*, 54, 205–220, 1990.

Fischel–Ghodsian et al., "Enzymatically Controlled Drug Delivery", *Proc Natl. Acad. Sci. USA*, 85, 2403–2406, 1988.

Bhave and Sirkar, "Gas Permeation and Separation with Aqueous Immobilized in Microporous Hydrophobic Hollow Fibers", *ACS Symp. Ser.* 347, 138–150, 1987.

Reid et al., *Properties of Gases and Liquids*, McGraw Hill Book Co., New York, 1977 (relevant pages).

Prasad and Sirkar, "Dispersion–Free Solvent Extraction with Microporous Hollow–Fiber Modules", *A.I.Ch.E.J.*, 34(2), 177–188, 1988.

*Primary Examiner*—Neil S. Levy
*Attorney, Agent, or Firm*—Law Offices of Jane Massey Licata

[57] ABSTRACT

A novel controlled release device employing microporous membranes with or without a nonporous coating and aqueous-organic partitioning of the bioreactive substances to be delivered is provided. Devices and methods for delivering pharmaceuticals, pest-control substances, hormones, nutrients and fragrances to humans, animals or any environment are also provided.

10 Claims, 8 Drawing Sheets

○ EXPERIMENTAL, WATER IN PORES
— PREDICTED, WATER IN PORES
— PREDICTED, ORGANIC IN PORES

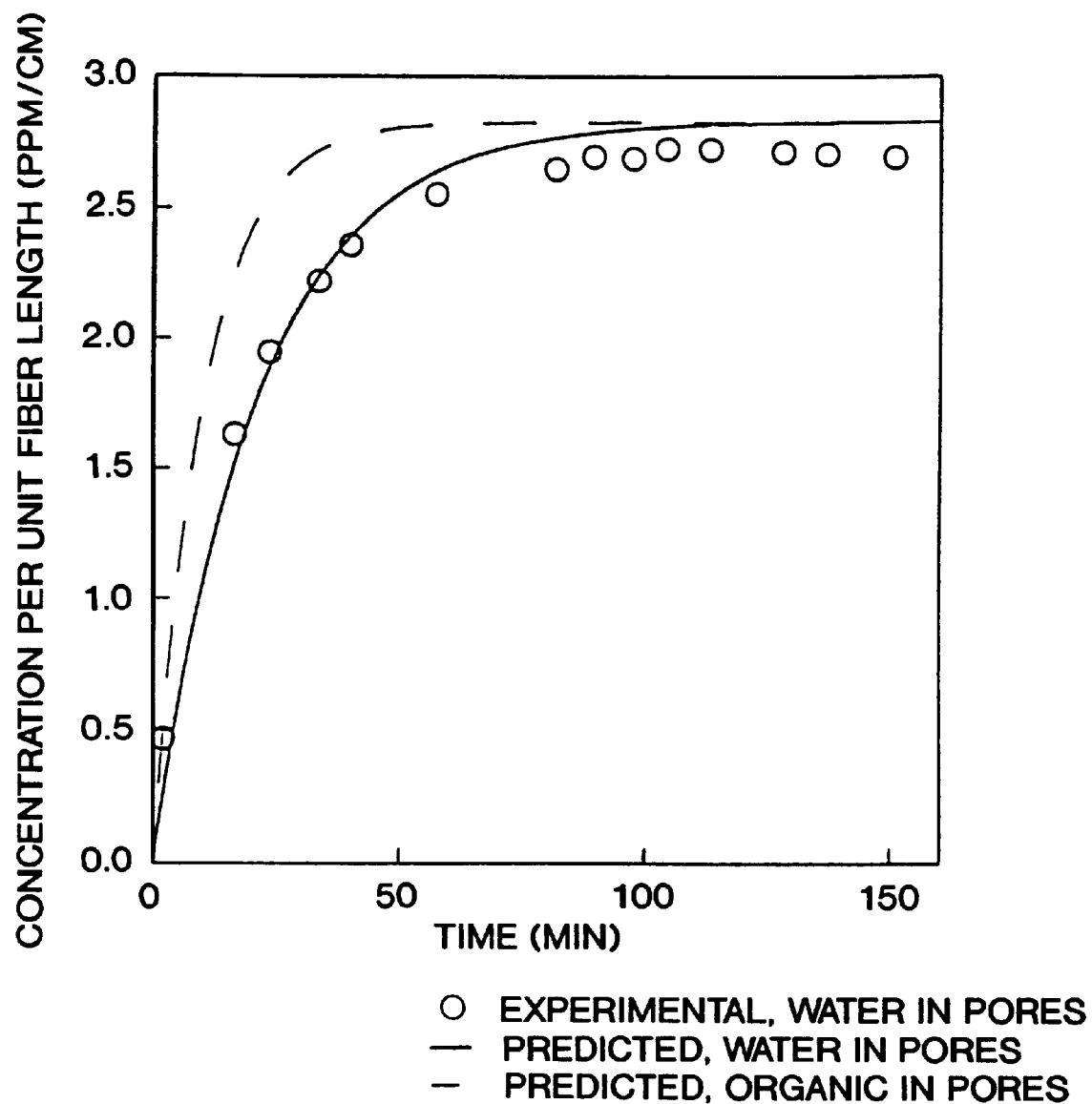

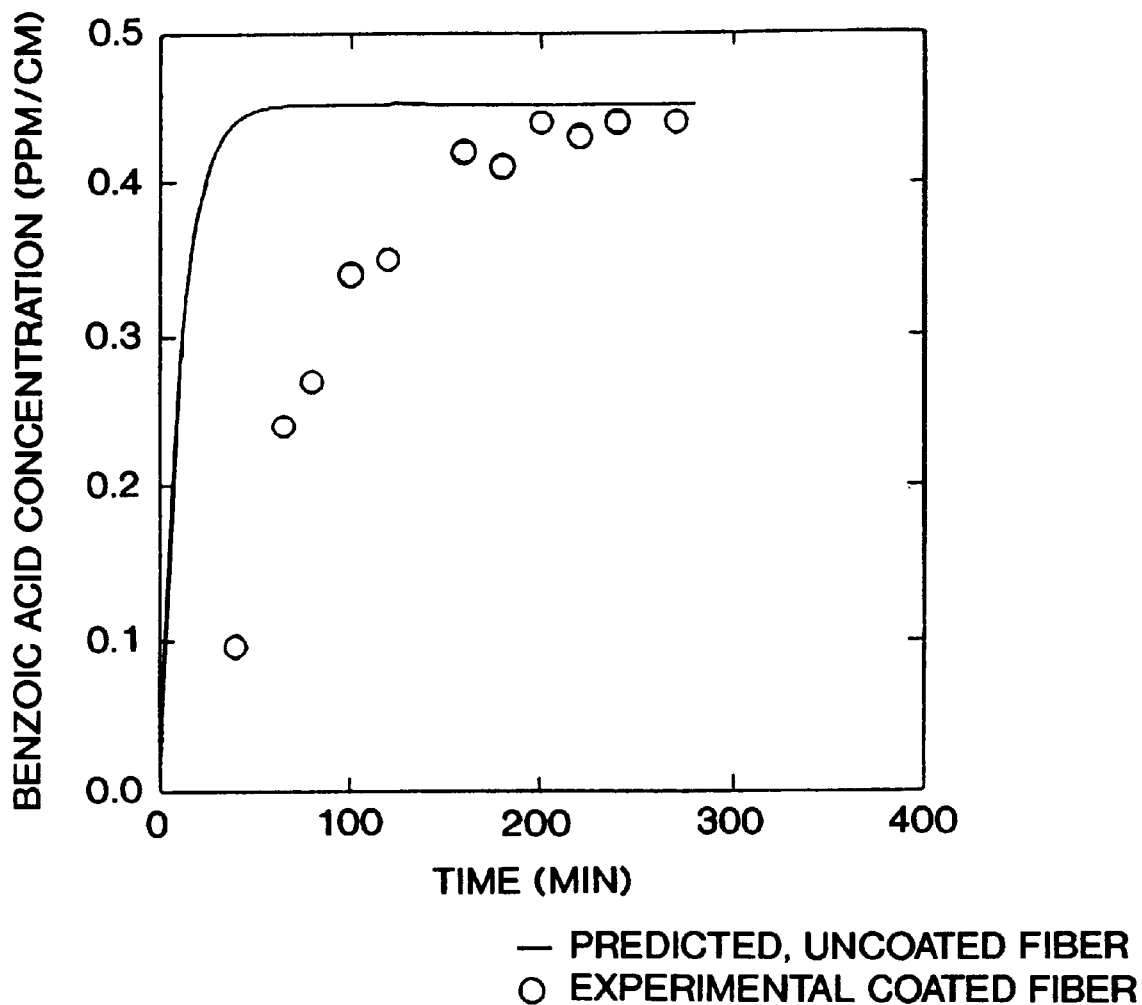

— PREDICTED, UNCOATED FIBER
O EXPERIMENTAL COATED FIBER WITH ADDITIONAL WAX COATING

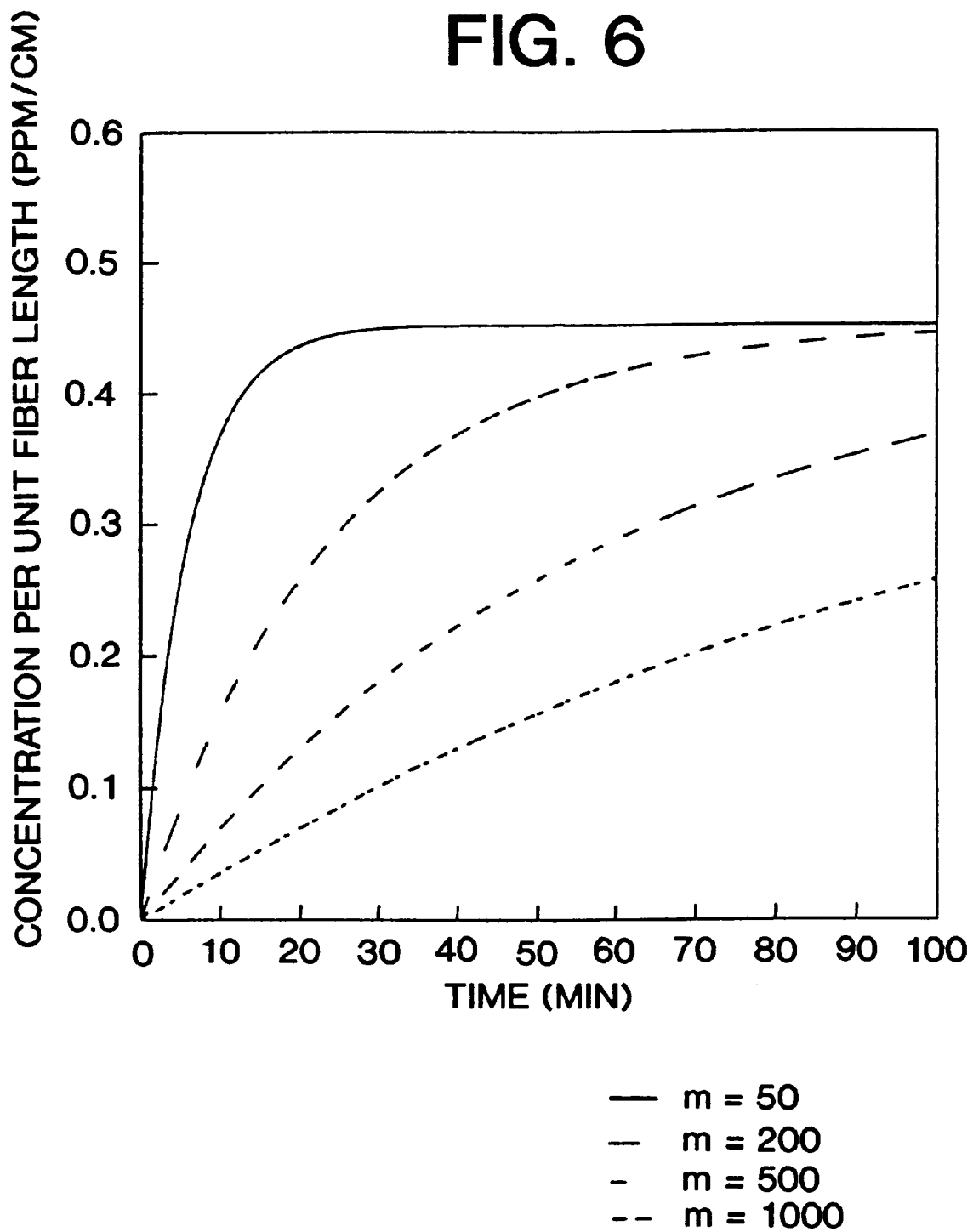

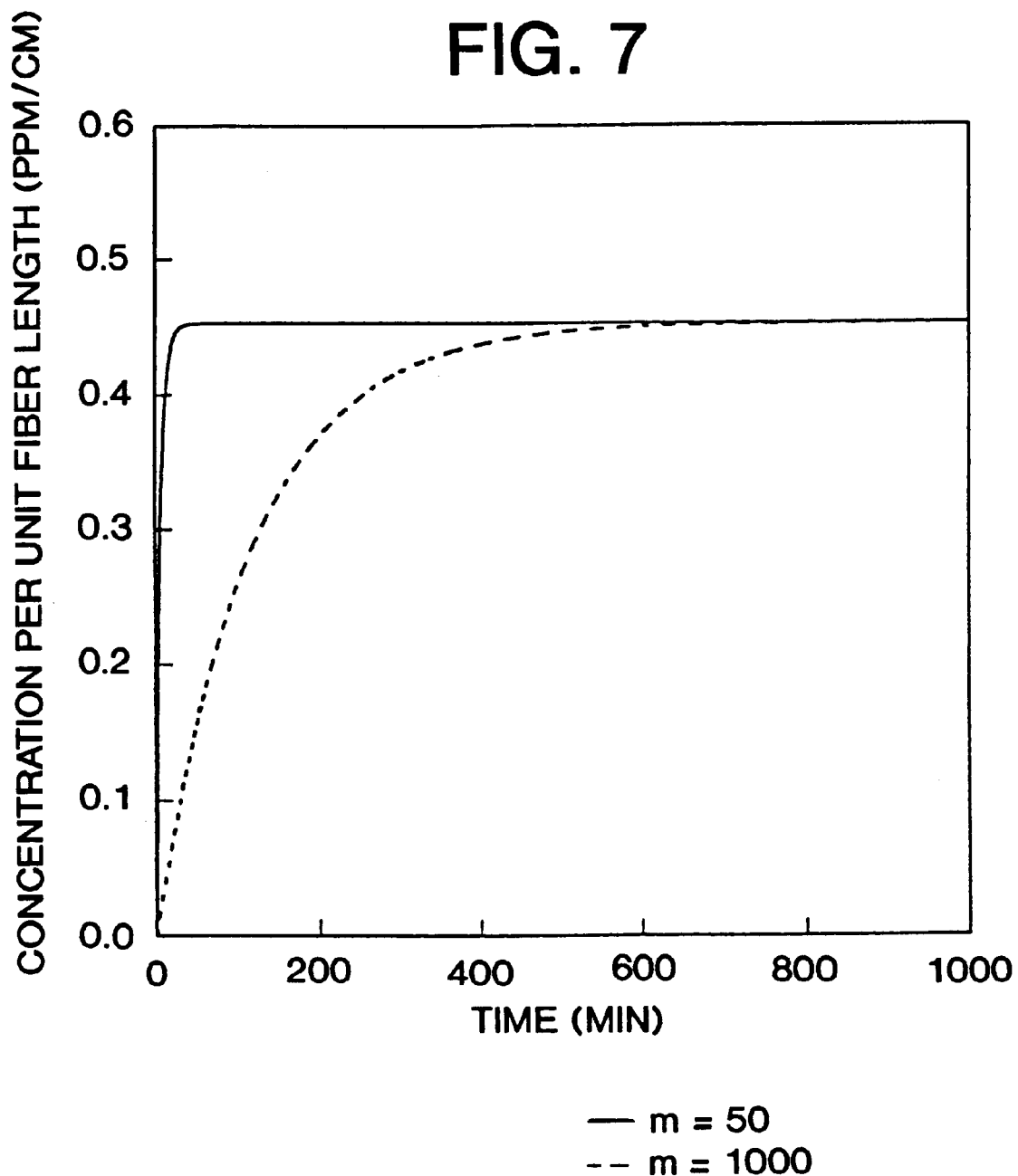

CONTROLLED RELEASE DEVICE BASED ON AQUEOUS-ORGANIC PARTITIONING IN POROUS MEMBRANES

BACKGROUND OF THE INVENTION

Scientists are continually searching for ways to manipulate biological factors to improve the well-being of mankind. In the pharmaceutical industry, this effort has focused primarily on finding new drugs to combat disease. While in agriculture, research has been directed toward finding new chemicals to control both disease and infestation. A new biological agent that is highly effective in vitro must be administered safely and effectively in vivo, often decreasing its practical efficiency. Until recently, the actual mechanism of delivery has received relatively little attention.

Common traditional methods of drug delivery include ingestion and injection. In either case, an initially concentrated form of the drug is rapidly diluted in a reservoir (either in the stomach or in the bloodstream) before it reaches its target. In this reservoir, the drug is also liable to removal by metabolism, excretion, or chemical degradation (for example, in the case of biosensitive materials such as proteins). From the reservoir, the agent may access organs or tissues other than the target which, even at low levels, may cause side-effects. For these reasons, the drug usually achieves a systemic concentration within the effective therapeutic range for only a short time between periods of toxicity and ineffectiveness.

A controlled release system delivers a drug at a specific rate for a definite period of time, the release kinetics being determined by the system design rather than by environmental conditions. This eliminates several of the disadvantages inherent in traditional methods of delivery, as the controlled release design offers the capability to maintain the drug level in the desired range, localized delivery to the target (lowering the systemic drug level), and preservation of biosensitive materials. Using such a device, a drug can be delivered more safely, effectively and economically.

Many of the controlled release devices that have been developed are polymeric systems. Langer, R., "New Methods of Drug Delivery", *Science*, 249, 1527–1533, 1990, provides an excellent review of these systems. A brief description of systems based on three mechanisms (diffusion, chemical reaction and solvent activation) that are capable of providing a constant rate of drug release is given below.

As an example of a diffusion-based system, consider a drug initially contained in a reservoir surrounded by a nonporous polymeric membrane. The drug must diffuse across the membrane and into the body, and the rate of release is controlled by the diffusivity of the drug in the membrane and the concentration difference of the drug across the membrane. If the drug is initially suspended in the reservoir, a constant thermodynamic activity of drug in solution can be maintained until all the suspended drug has dissolved and diffused out, effecting zero order release kinetics for this time period, provided the rate of solute dissolution is faster than the rate of diffusion. A variation on this concept is the matrix device, in which a drug is initially dissolved or dispersed in the polymer itself, so that the polymer serves both as a reservoir and membrane. For example, Norplant™ is a subdermal reservoir device that is capable of releasing contraceptive for 5 years and has been approved for use in a number of countries.

A matrix device using a polymer that can be chemically degraded by the surrounding environment is a system that is controlled by chemical reaction. The polymer can display either bulk erosion or surface erosion, the latter being more useful when maximum control over release is desired. A surface erodible polyanhydride disk containing nitrosoureas for treatment of brain cancer after surgery is currently being tested in a placebo-controlled clinical trial.

In a solvent activation system, a constant (or increasing) rate of release may be achieved using a matrix device in which polymer swelling is caused by environmental conditions. As the polymer swells, its dimensions increase, as does the diffusivity and the ratio of solubility to concentration of drug in the matrix, thereby compensating for the decrease in thermodynamic activity caused by loss of drug. Vyavahare et al., "Zero Order Release from Glassy Hydrogels. II Matrix Effects", *J. Membrane Sci.*, 54, 205–220, 1990, have achieved zero order release kinetics for benzoic acid and theophylline from such a hydrogel system.

Sometimes it is not a constant release rate that is desired. Certain substances, such as insulin, which are normally produced by the body, would ideally be administered only as the body needs them. Fischel-Ghodsian et al., "Enzymatically Controlled Drug Delivery", *Proc Natl. Acad. Sci. USA*, 85, 2403–2406, 1988, have developed a system for pulsatile controlled release which is used to mimic the body's physiological process of insulin secretion. The device consists of beads on which glucose oxidase is immobilized, surrounded by a polymer matrix containing insulin. Glucose from the surroundings diffuses into the matrix to react with the glucose oxidase on the beads, forming gluconic acid as a product. As gluconic acid diffuses back out through the matrix, the pH in the matrix decreases. The decrease in pH lowers the solubility of insulin in the matrix, forcing the release of insulin. The resulting decrease in glucose level (as a result of increased glucose metabolism) is detected by the controlled release device, and insulin secretion ceases.

It is evident that a controlled release device using a porous hollow fiber has advantages over the conventional polymeric membrane devices. By careful selection of the solvent/solute/membrane system, enormous flexibility in the rate of release of a selected agent can be achieved, and the porous hollow fiber which is designed to be a highly efficient mass transfer device can be used as a rate controlling device.

SUMMARY OF THE INVENTION

The invention is a new controlled release device and method employing porous membranes with or without a nonporous coating and aqueous-organic partitioning of the selected agent to be delivered. The porous membranes are primarily in hollow fiber form but can also have the form of a flat film. Microporous membranes are preferred. The invention may be used to deliver selected agents such as pharmaceuticals, pest-control substances, hormones, nutrients and fragrances to humans, animals or any environment, gaseous, aqueous or organic. The invention may be used in the form of a single, chopped hollow fiber with sealed ends or in a tape form of multiple hollow fiber dispenser, or as a flat dispenser having a flat film attached to a flat-ended reservoir. Such a device is attached to the body of the human or animal subject as a patch or dispersed over foliage for insect control or attached to any physical environment for controlled release of bioactive substances. Using biocompatible or biodegradable materials for membranes and biocompatible solvents, the invention may be used as an implant or ingestible substance for controlled release of drugs.

BRIEF DESCRIPTION OF THE DRAWINGS

FIG. 3 is a graph showing the controlled release of benzoic acid using Nylon-6 600 μm I.D. microporous hollow fibers.

FIG. 4A is a graph showing the controlled release of benzoic acid using 1 μm silicone-coated Celgard® 240 μm I.D. microporous hollow fibers.

FIG. 6 is a graph showing the effect of distribution coefficient on the release of benzoic acid from Celgard® X-20 240 μm microporous hollow fibers.

FIG. 7 is a graph showing the effect of distribution coefficient on the release of benzoic acid from Celgard® X-20 240 μm microporous hollow fibers.

DETAILED DESCRIPTION OF THE INVENTION

Figure 1:
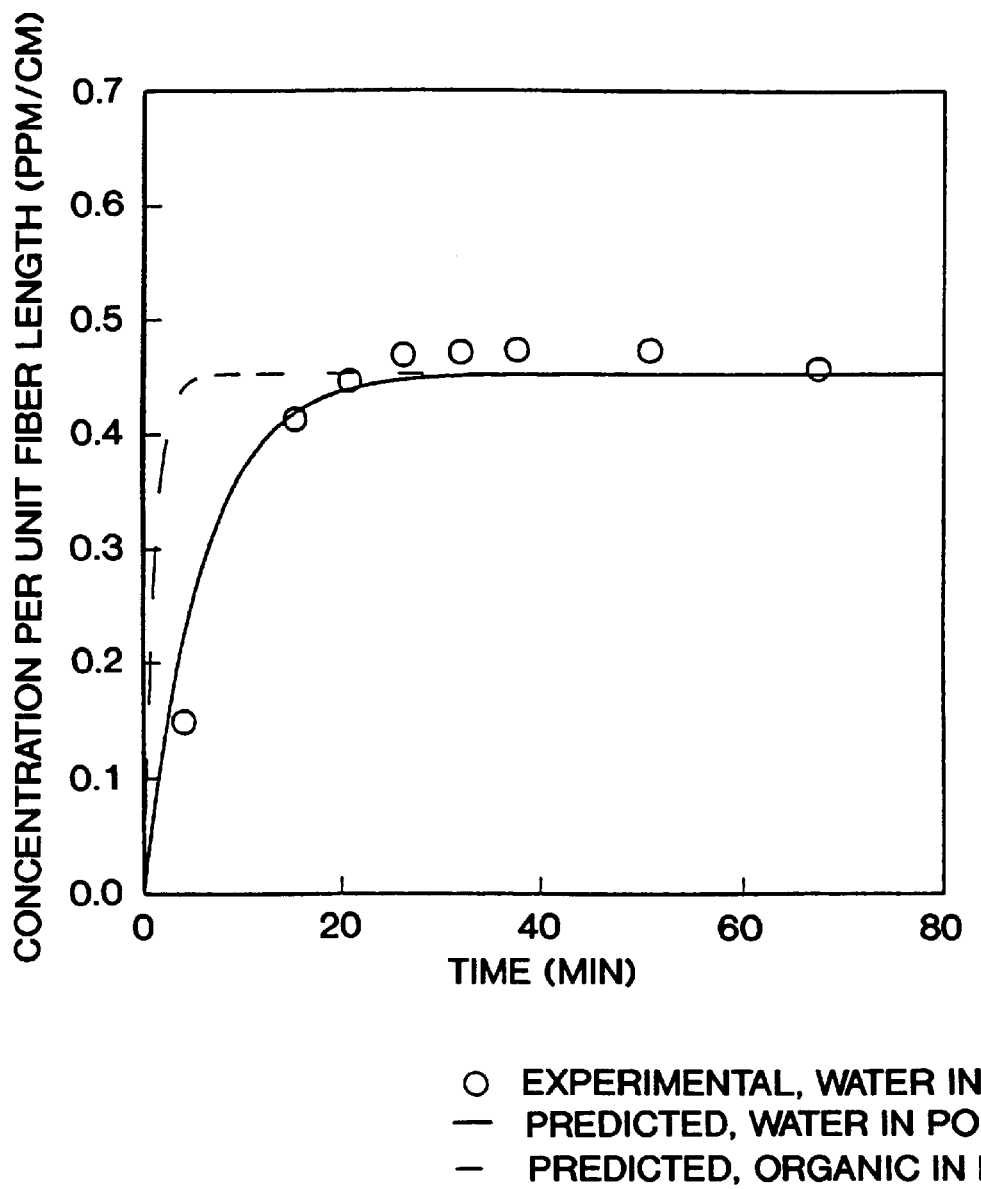
FIG. 1 is a graph showing the controlled release of benzoic acid using Celgard® X-20 240 μm I.D. microporous hollow fibers.

Controlled release of compounds from a variety of controlled release products can be mediated by nonporous or porous membranes. The invention is a novel controlled release technology that uses porous membranes, preferably microporous membranes, in hollow fiber or flat membrane form. In some embodiments, multiple compounds are released by multiple fibers. The technology is particularly useful for sustained delivery of substances which have limited solubility in aqueous media. The technology does not require dispersing the compound or formulation in a polymeric matrix and then releasing it to the environment (either by matrix erosion, permeation through a polymer membrane, or partitioning from the matrix to an aqueous solution). Fabrication of the polymer matrix filled with a selected agent, which is often a major manufacturing step, is not needed. A zero-order release is also easily assured in the present invention.

In one embodiment, a short length of a porous hollow fiber containing the selected agent in an organic solvent in the fiber lumen is employed. The pores of the wall of the hollow fiber contain water or an appropriate aqueous solution. Further, the two ends of the fiber lumen can be sealed with appropriate sealant or heat-sealed. Such a chopped hollow fiber is then applied by means of a backing with appropriate adhesive to any surface intended for delivery of a pharmaceutical, pest-control substance, hormone, nutrient or fragrance, referred to herein as a "selected agent". The agent present in the organic solvent in the fiber lumen will partition into the water or aqueous solution in the fiber pores and then diffuse through the pores to the fiber exterior surface for release to the desired surface on which the controlled release device rests. In another embodiment, the fiber contains the selected agent in water. The pores of the wall of the fiber contain an organic solvent.

Many substances which are useful selected agents have very high solubility in organic solvents. On the other hand, many such substances have very low solubility in water. The solubility in water may sometimes be enhanced by appropriate pH changes or other additives. If the selected agent has a very low solubility in water, then partitioning of the agent from the organic solvent in the fiber bore to the water in the pores of the fiber wall will hardly affect the agent concentration in organic solvent. The organic solvent will essentially act as an infinite reservoir for the selected agent. Thus, the selected agent's concentration in water at the water-organic interface in the pore mouth of the fiber inside diameter will remain constant with time over long periods of time. This ensures, de facto, zero order release as the selected agent diffuses out through the water-filled pore to the surface, where it is to be applied under a constant concentration gradient. In other embodiments, a tape form containing multiple fibers is provided. Multiple fibers containing different selected agents are also useful in some embodiments of the invention.

The organic solvent selected to solubilize the selected agent and to act as a reservoir for the agent will be partially soluble in the aqueous phase in the pores of the hollow fiber wall. It is preferable to select a solvent with as low a solubility in water as possible. It is also desirable to select an organic solvent with no influence on the agent or its metabolism in the host body. In other embodiments, the selected agent is solubilized in water and the pores in the fiber wall contain an organic solvent.

If the selected agent is to be delivered to ambient atmosphere having considerable potential for volatilizing the water in the pores of the hollow fiber wall, it is preferred that water or organic solvent in the pore wall is gelled by the addition of appropriate gelling agents. This will reduce the rate of agent delivery while preserving the controlled release system structure. Alternatively, a substantially moisture impermeable coating of, for example, wax, may be applied on the outside surface.

In another embodiment, a flat impermeable backing is employed. The agent solution in organic solvent or water may be kept on top of it and enclosed by a microporous flat film whose pores will contain water or organic solvent or a gel, as appropriate.

The techniques employed in the controlled release inventions provided here may be used to deliver nutrients, pharmaceuticals, hormones and pest-control substances (referred to herein as a "selected agent") to animals, humans, or any gaseous or aqueous environment. Insect growth regulators like methoprene, insecticides like fenvalerate, pheromones like Z7DDA ((Z)-7-dodecenyl acetate) and pesticides like Temephos are specifically contemplated in the present invention. Sustained release of antigens or hormones or peptides is contemplated in additional embodiments of this invention.

In some methods of the invention, a drug delivery device may be administered by any convenient route. Various delivery systems are known. These include encapsulation in liposomes, microparticles or microcapsules. Other methods of introduction include, but are not limited to, intradermal, intravenous, intranasal and oral routes.

The present invention is a novel diffusion-limited reservoir type polymeric controlled release device. The rate controlling mechanism is based on the partitioning of the solute between an aqueous and an organic phase. The device employs porous hollow fibers, preferably microporous fibers, as the polymeric membrane. The reservoir is contained in the lumen of the fibers. The geometry of the hollow fiber naturally lends itself to this type of reservoir device, and the porous membrane provides several advantages over the conventional nonporous membrane devices.

In a diffusion-limited polymeric controlled release system using a nonporous membrane surrounding a reservoir, the release kinetics are controlled primarily by the concentration of the selected agent in solution, the solubility of the selected agent in solution and in the membrane, and the diffusivity of the selected agent in the membrane. Many high molecular weight nonpolar agents have significant solubility in a polymeric membrane material such as silicone, a factor which is undesirable when a slow rate of release is needed. The same agent, however, is likely to have an extremely low solubility in water. If water is immobilized in the pores of the microporous hollow fiber, the rate of release of the agent can be effectively decreased. The diffusivity of the agent in water is greater than that of the agent in a nonporous polymer membrane, however, this effect is compensated for by the porosity and tortuosity of the porous membrane whose pores are filled with water. In addition, a large molecule such as a protein molecule will be likely to exhibit hindered diffusion due to interactions with the pore walls.

In other embodiments, a much larger quantity of the selected agent can be incorporated by using a saturated solution of the agent in the solvent in the fiber lumen which, in addition, has fine particles of the agent suspended in the solution. Thus, the solution is supersaturated with crystals or particles in suspension. As the agent is released, its concentrations in the organic and aqueous phases do not decrease with time over a considerable interval of time since the suspended particles dissolve in the organic solvent as needed to keep it saturated. This ensures virtually zero order release (i.e., a constant release rate) which is often desired in controlled release applications. The duration of such zero order release is also considerably lengthened. Only when the solution becomes less than saturated, does the release rate of the selected agent begin decreasing.

If it is desired to extend the duration of such zero order release even further, the porous hollow fiber or flat membrane utilized may be chosen such that it has a nonporous polymeric coating on the fiber outside diameter. Being an additional transport resistance of significant value, such a nonporous coating will reduce the magnitude of the rate of release of the drug, thereby extending the duration of zero order release period.

The microporous membrane chosen may be symmetric or asymmetric. An asymmetric membrane, chosen such that the pore diameter over a small thickness of the membrane is much smaller than that in the rest of the membrane, can hinder the diffusion of the selected agent if the smaller pore dimension is no larger than that of the solute by an order of magnitude. Such an asymmetric membrane structure can decrease the agent release rate even further, especially for relatively large agent molecules. This can extend the duration of zero order release considerably.

A variety of microporous hollow fibers can be used for the controlled release objectives of the instant invention. Table 1 provides a partial listing of such hollow fibers. Membranes with similar porosity and pore sizes are also available in flat form and can be used as such. Hydrogel hollow fibers of regenerated cellulose (e.g., Cuprophan®) or other materials, as well as flat films, are equally useful for the present invention. The pore sizes may be as low as 1 nm or as large as 10 $\mu$m.

Microporous hollow fibers can be hydrophobic or hydrophilic. The pores in the wall of the hollow fibers are filled with water or an aqueous solution in the present invention. For hydrophilic fibers, this is achieved by immersing the fiber in a bath of water or aqueous solution. For microporous hydrophobic fibers, on the other hand, a special exchange process is necessary. For example, Bhave and Sirkar, *ACS Symp. Ser.* 347, 138–150, 1987.

In either case, each hollow fiber is inserted first into a B-D Precision Glide™ needle up to a distance of about ½ to 1 inch and the union of the fiber and needle affixed to a microscope slide using a large drop of RTV silicone rubber adhesive/sealant (General Electric, Waterford, N.Y.) which is later cured. For hydrophilic fibers, wetting is achieved by immersing the fiber in water while injecting water into the lumen.

For hydrophobic fibers, the initial wetting is done with 80 vol % ethanol in water as the fiber-needle assembly is kept above the solution. The 80 vol % ethanol in water solution is gradually changed to pure water over a period of 36 hours. The bath water is injected into the fiber bore periodically.

An organic solution of the selected agent is injected next into the bore of either kind of hollow fiber after first injecting water into the fiber bore to remove air bubbles, if any. A certain length of such fiber is then cut out and the two ends are sealed. A variety of sealing methods may be adopted. The fiber ends may be heat-sealed (especially for thermoplastics like polypropylene (PP)) or molten wax or molten polypropylene or polyethylene (PE) may be applied quickly to seal each fiber end as the molten wax/PP/PE cools.

For commercial production purposes, a number of methods may be adopted. For example, a standard shell-and-tube exchanger type of hollow fiber module assembly may be used. After wetting the fiber pores spontaneously, or by an exchange process, or by using an excess aqueous solution pressure in the lumen to force it through the pores, the fiber lumen should be filled with the agent-containing solution from the tube-side of the device. The shell of the hollow fiber device should then preferably be removed. The fiber assembly then may be chopped off at the tubesheet. One end of the fiber bundle may then be flared a little to create distance between individual fibers and heat-sealed. Alternatively, the fibers in the flared bundle could be sealed by application of molten wax. The same procedure is to be adopted for the other end of the fiber.

For microporous hydrophobic fibers having a nonporous polymeric coating of silicone (or other suitable material), the wetting procedure should employ 80 vol % ethanol in water in the fiber bore to start with. This is to be gradually replaced over a period of 36–48 hours by solutions of lower ethanol concentration until pure water is used. The rest of the procedures are similar to those adopted for other fibers.

Hollow fibers prepared as such may then be assembled in any fashion intended for controlled release purposes. Preliminary testing of the release kinetics of a selected agent is carried out by immersing a length of the hollow fiber with sealed ends in a stirred water bath and measuring the concentration of the agent in the water bath as it increased with time.

In preliminary tests of the aqueous-organic solute partitioning system of the invention in microporous hollow fibers, rate-controlling parameters were identified, and their effect on the release kinetics determined. This was facilitated by use of a mathematical model.

Analytical solutions for non-coated, wetted fibers and for non-coated, non-wetted fibers were developed to predict the aqueous phase benzoic acid concentration as a function of time for nylon fibers as well as Celgard® X-20 200 $\mu$m and 400 $\mu$m I.D. fibers, both wetted and non-wetted. Predicted results were compared with experimental data (for wetted fibers only) in FIGS. 1, 2 and 3 for Celgard® X-20 240 $\mu$m I.D., Celgard® X-20 400 $\mu$m I.D. and Nylon 6 600 $\mu$m I.D. fibers, respectively. The hollow fiber dimensions and membrane porosities were supplied by the manufacturer. In the case of the silicone coated fibers, the coating thickness was estimated experimentally. The diffusivity of benzoic acid in decanol was estimated using the Wilke-Chang Equation. The diffusivity of benzoic acid in water was taken from Reid et al., *Properties of Gases and Liquids*, McGraw Hill Book Co., New York, 1977. Hydrophobic membrane tortuosities were taken from Prasad and Sirkar, "Dispersion-Free Solvent Extraction with Microporous Hollow-Fiber Modules", *A.I.Ch.E.J.*, 34(2), 177–188, 1988, whereas the tortuosity of the Nylon 6 membrane was assumed to be unity, since the pore size is so large. The values of the parameters used in this model are given in Table I. The distribution coefficient (m) for benzoic acid between water and decanol was estimated to be 50. The distribution coefficient is the ratio of equilibrium solute concentration in organic solvent over that in water.

TABLE I

Parameters used in controlled release model.

| FIBER | CELGARD ® X-20 | CELGARD ® X-20 | NYLON 6 |
|---|---|---|---|
| inside radius (cm) | 0.0120 | 0.0200 | 0.0300 |
| outside radius (cm) | 0.0145 | 0.0225 | 0.0500 |
| tortuosity | 2.5* | 2.5* | 1.0** |
| porosity | ~0.4 | 0.4 | 0.75 |
| diffusion coefficient in water (cm$^2$/s) | | $1.2 \times 10^{-5}$*** | |
| diffusion coefficient in solvent (cm$^2$/s) | | $1.3 \times 10^{-6}$**** | |
| distribution coefficient | | 50 | |

Figure 2:
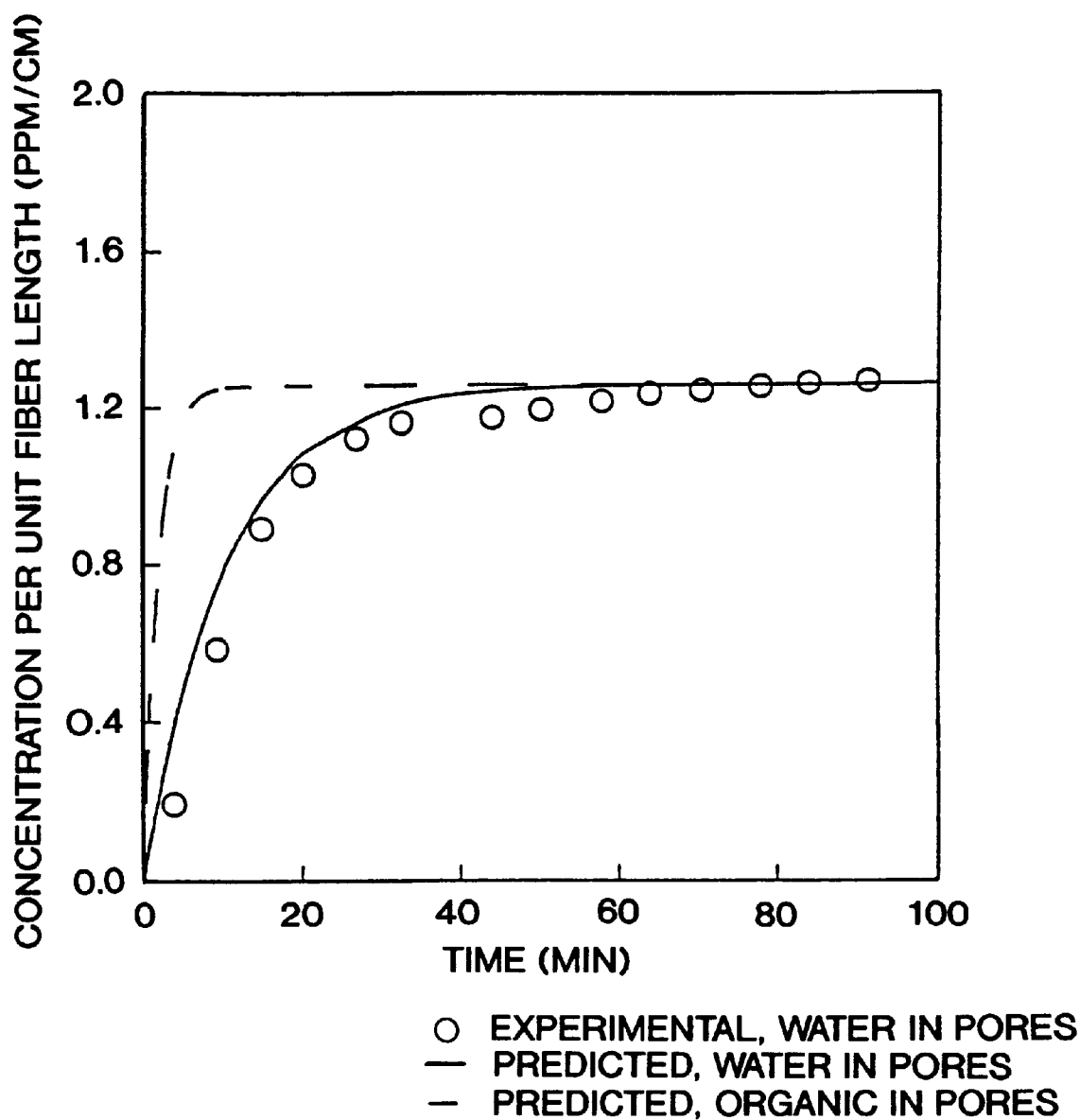
FIG. 2 is a graph showing the controlled release of benzoic acid using Celgard® X-20 400 μm I.D. microporous hollow fibers.

*From Prasad and Sirkar, 1988
**Assumed to be 1.0 because pore size is large
***From Reid et al., 1977, p. 576
**Calculated from Wilke-Chang Equation As shown in FIGS. 1, 2 and 3**, the model is indeed useful, as the predicted concentrations for wetted fibers (solid lines) agree well with the experimental data for both the 240 and 400 µm I.D. hydrophobic and the Nylon 6 hydrophilic microporous hollow fibers.

Despite the close agreement between the predicted and experimental concentrations, there are several other factors to be considered. In the case of the hydrophobic fibers (which are filled with organic solution while submerged in water and then cut into segments, sealed, and placed in the aqueous solution one at a time), some loss of solute to the bath in which the fibers are kept wet before they are placed in the aqueous solution is expected. This would effect a lower than predicted initial release rate as well as a lower steady state solute concentration due to a smaller quantity of solute present in each fiber segment as it is placed in the aqueous solution. This effect could be masked by the presence of some organic solution in the pores initially, although an effort was made to inject the solution gently into the lumen, the pressure difference across the fiber wall could push some of the organic into the pores, increasing the amount of solute initially introduced into the fiber, and compensating for the effect of solute loss.

The rate of release depends on the fiber wall thickness, effective diffusivity, and solute distribution coefficient between lumen and the pore liquid.

Figure 4B:
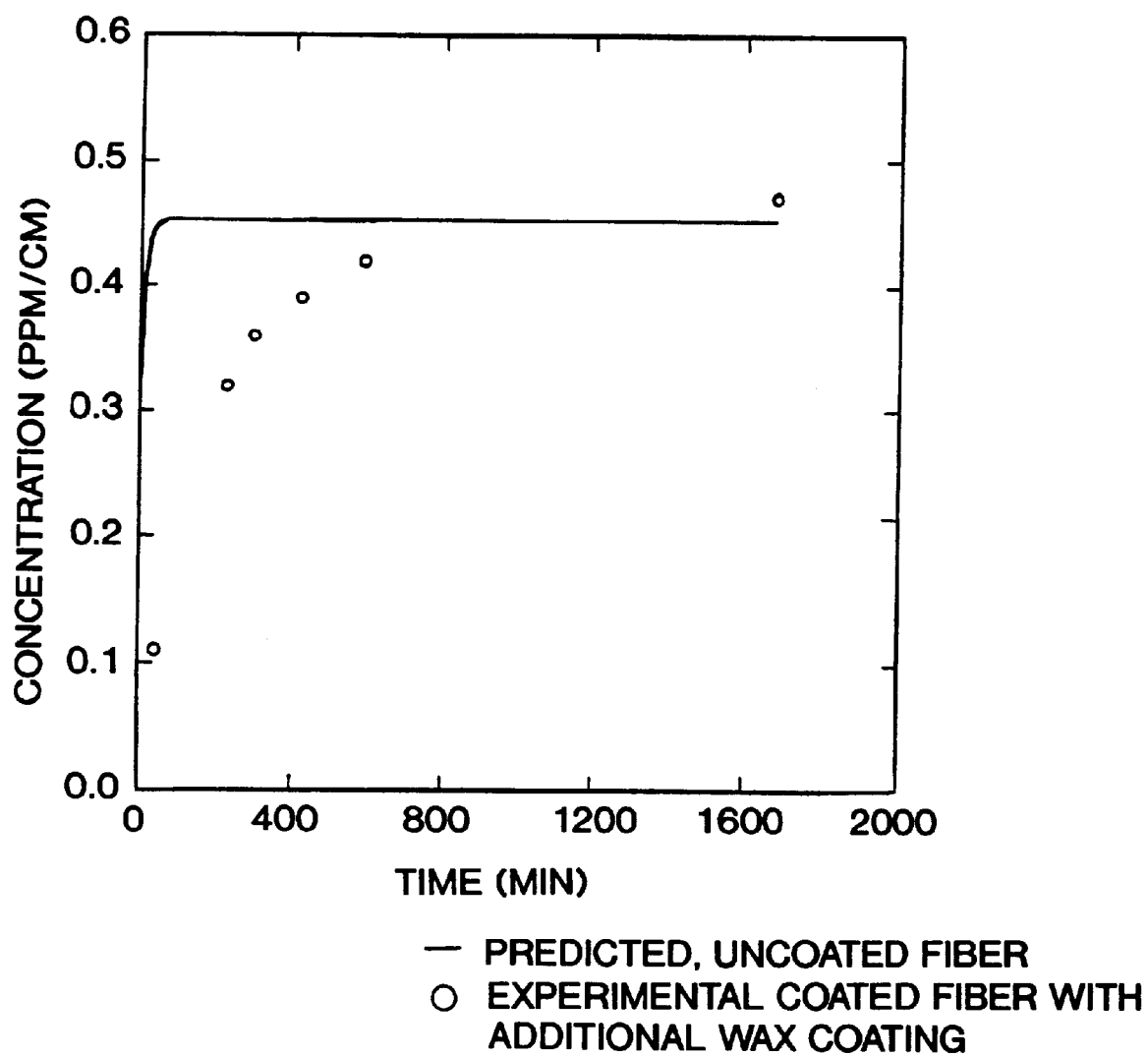
FIG. 4B is a graph showing the controlled release of benzoic acid using 1 μm silicone-coated Celgard® 240 μm I.D. microporous hollow fibers, with an additional wax coating.

A coating on the outer surface of the fiber provides additional resistance to mass transfer. Comparison of the experimental data for the coated fibers to predicted concentrations for the same fibers, uncoated, reveals that the coating increases the time required for the system to approach steady state. The controlled release of benzoic acid using silicone-coated hollow fibers (with and without an additional wax coating) and octanol is shown in FIGS. 4A and 4B. For both Figures, the predicted results are based on a 240 µm uncoated fiber with the same membrane thickness, porosity and tortuosity. In FIG. 4A, a 240 µm Celgard® fiber was coated with a 1 µm silicone coating. In FIG. 4B, a 240 µm Celgard® fiber was coated with a 1 µm silicone coating, and an additional wax coating. In both experiments, the solvent was octanol and the diffusing species, benzoic acid.

Figure 5:
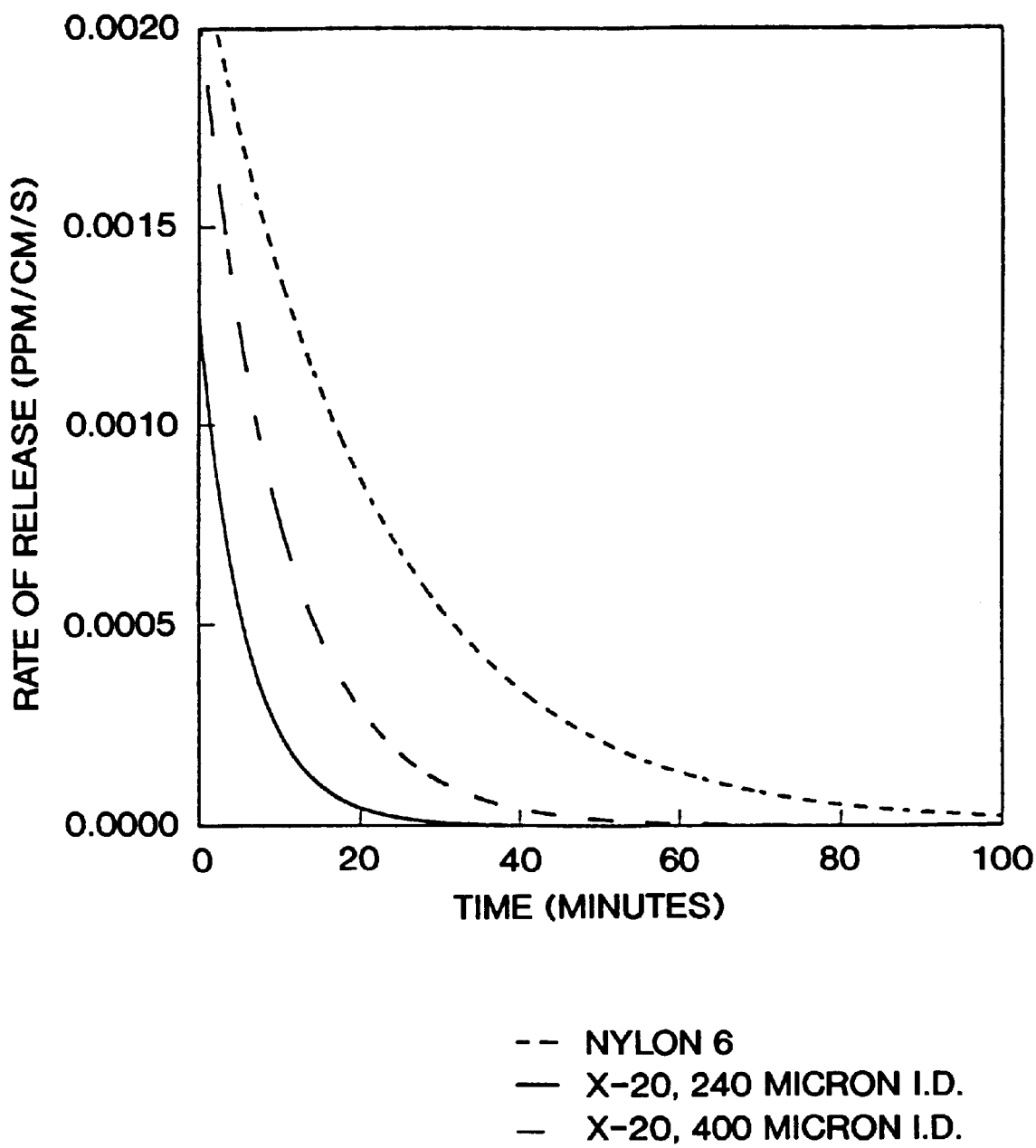
FIG. 5 is a graph showing the predicted rate of release of benzoic acid from Celgard® X-20 240 and 400 μm I.D. and Nylon-6 microporous hollow fibers.

In controlled release technology, it is the rate of solute delivery that is of primary importance. While achievement of zero order kinetics was not an objective here, it is, however, worthwhile to examine the experimental release rates that were achieved by immobilizing water in the pores of the hollow fibers whose lumen had the solvent containing the solute. FIG. 5 shows the predicted release rate as a function of time for each fiber used.

The potential to manipulate the rate of solute release from the controlled release device is desirable and necessary. Typically, it would be desirable to achieve zero order release kinetics with a slow rate of release. In order to obtain such controlled release of the solute, the system parameters must be manipulated, as discussed below.

For a given solute/solvent/fiber system, the maximum rate of release obtained (theoretically at time equal to zero, when the solute concentration in the organic solvent is near the saturation level) can be achieved for an extended period of time by introducing a suspension into the hollow fiber lumen initially. Provided the rate of dissolution of the suspended drug into the organic solvent is faster than the rate of diffusion of the solute out of the lumen, the saturation level solute concentration can be maintained for an extended time, effecting zero order release kinetics.

The release rate for a given solute/fiber combination can be manipulated by selection of organic solvent. The model predicts that the release rate is inversely proportional to the distribution coefficient. FIGS. 6 and 7 show the predicted release rate as a function of time, with the distribution coefficient as a parameter, for times less than 100 minutes and times of up to 1000 minutes, respectively. These data show the tremendous flexibility of release kinetics attainable by variation of one parameter of a hollow fiber controlled release device.

A technique for using the aqueous-organic solute partitioning system using a porous hollow fiber as a controlled release device has been developed. The technique proved successful, and experimental data matched model predictions well. By comparison of theoretical predictions for solute release through organic-filled pores with experimental data for fibers with water-filled pores, it was demonstrated that the rate of solute release can be significantly decreased simply by increasing the solute distribution coefficient between the liquid in the lumen and that in the pores. This demonstrates that this system has considerable potential as a controlled release device.

The invention is further illustrated by the following, non-limiting examples.

EXAMPLES

Example 1

Materials and Methods of Analysis

Benzoic acid and decanol were obtained from Aldrich Chemical Company (Milwaukee, Wis.), and were both used as received. Octanol was received from Fisher Scientific (Springfield, N.J.) and was used as such. The fibers used were hydrophilic nylon fibers from ENKA America, Inc. Technical Membrane Group (Asheville, N.C.), Celgard® hydrophobic polypropylene X-20 240 $\mu$m and 400 $\mu$m inner diameter (I.D.) fibers from Hoechst Celanese Separations Products Division (Charlotte, N.C.), and silicone-coated 100 $\mu$m and 240 $\mu$m I.D. hydrophobic polypropylene fibers from Applied Membrane Technology Inc. (Minnetonka, Minn.). Physical characteristics of these fibers are given in Table II.

TABLE II

Physical properties of hollow fibers used*

| HOLLOW FIBER | MATERIAL | PORE SIZE $\mu$m | POROSITY | OD $\mu$m | ID $\mu$m | COATING THICKNESS $\mu$m |
|---|---|---|---|---|---|---|
| Celgard ® X-20 (hydrophobic) | Polypropylene | 0.03 | 0.4 | 290 | 240 | |
| Celgard ® X-20 (hydrophobic) | Polypropylene | 0.03 | 0.4 | 450 | 400 | |
| Silicone-coated (hydrophobic/silicone) | Polypropylene/ silicone | 0.03 0.03 | 0.2 0.4 | 140 290 | 100 240 | 1** 1** |
| Nylon 6 (hydrophilic) | Polyamide 6 | 0.2 | 0.75 | 1000 | 600 | |

*Information supplied by manufacturer
**Estimated experimentally

Aqueous phase benzoic acid concentration was analyzed by a Hewlett-Packard HPLC model 1090, using a Hypersil ODS C-18 reverse phase column. A 40% acetonitrile –60% water (w/w) carrier and UV detector at 254 nm were used. The samples were injected manually into a 100 $\mu$m sample loop. A calibration curve for benzoic acid concentration as a function of area count was prepared. The distribution coefficient of benzoic acid between decanol and water was determined experimentally.

Example 2

Fiber Preparation

Fibers were cut into lengths of approximately 30 cm (except for the nylon fibers which were available only in 15 cm segments). One end of a fiber was carefully inserted into an appropriate size B-D® Precision Glide™ needle (Becton Dickinson, Rutherford, N.J.), so that the end of the fiber extends about 2 cm into the needle but is not visible at the other end of the needle. The union of the fiber and needle was then affixed to a microscope slide using a large drop (about 1.5 cm in diameter) of General Electric (Waterford, N.Y.) RTV Silicone rubber adhesive/sealant, and allowed to cure for 24 hours.

Example 3

Wetting Procedure

Fibers were wetted with water after being connected to needles and fixed in a glass slide. Hydrophobic fibers were initially wetted with 80% (v/v) ethanol in sterile deionized water in an oblong pyrex vessel. The glass plates to which the fibers were affixed were suspended above the liquid level and kept dry throughout the procedure. The ethanol was gradually exchanged with sterile deionized water over a period of 36 hours as follows. After 9 hours, water was added to the bath to dilute the ethanol to 60%; after another 9 hours, the concentration was diluted to 40% and so on. The liquid level was reduced by removing solution when necessary to keep the glass slides dry. The final step involved removing all of the solution and replacing it with pure sterile deionized water. After each addition of sterile water to the surrounding bath, the bath solution was injected into the fiber lumen using a 3 cc B-D® sterile disposable syringe. Hydrophilic fibers were wetted without exchange by immersing them in a sterile deionized water bath for about 3 minutes while injecting water into the lumen.

Example 4

Injection of Solute and Solvent into Fiber Lumen

Immediately prior to filling the fiber lumen with the solution of the organic solvent containing the solute, water was injected into the bore to ensure the absence of air bubbles that occasionally become trapped on the surface of the fiber beneath the surface of the water. The syringe was detached from the needle and replaced by another containing about 2 cc of a solution of 2.5 mg benzoic acid in 25 ml decanol. The solution was gently pushed through the bore of the fiber, using minimum pressure to avoid breakthrough of the organic phase. In the case of wax-coated fibers, the fiber was coated by dipping the length of fiber in melted wax prior to injection of solute and solvent into the fiber bore.

Example 5

In Vitro Release Studies

After a fiber was filled with the organic solvent and solute, a segment of length between 5 and 8 cm was cut from the end. The ends were sealed with melted wax (ordinary candle wax, red color to enhance visibility; nylon fibers were sealed with melted polypropylene beads), and the fiber was immersed in 100 ml sterile deionized water contained in a covered cylindrical glass vessel (Corning Glass, Corning, N.Y.). This cutting and sealing procedure was repeated until all but the last 5 cm (approximately) of the fiber had been used. In order to provide a total fiber length long enough to achieve measurable and reproducible aqueous phase concentrations in the vessel during the experiment, sometimes it was necessary to fill, cut and seal two fibers. Samples were taken at 5.5 minute intervals from the aqueous phase in the glass vessel until the benzoic acid concentration remained constant (within 5%) for three successive measurements. Two additional samples were then analyzed at 15 to 20 minute intervals to ensure that a steady state had been achieved. After the experiment was stopped, the fibers were removed from the vessel and their lengths measured. Experiments were performed using each type of fiber mentioned above; all fibers were used with water in the pores.

What is claimed:

1. An aqueous-organic partitioning-based, diffusion-limited reservoir-containing controlled release device comprising a microporous membrane consisting of a hollow fiber having sealed ends or a film attached to a flat-ended reservoir wherein pores extending through the microporous membrane wall are 1 nm to 10 $\mu$m in size and are filled with water or an organic solvent and the fiber lumen or reservoir is filled with an organic solvent or water and a pharmaceutical so that the pharmaceutical in the fiber lumen or reservoir partitions into the water or organic solvent in the pores and diffuses through the water or organic solvent in the pores and out of the microporous membrane.

2. The device of claim 1 further comprising a nonporous coating on the membrane's outer surface.

3. The device of claim 2 wherein the coating comprises a polymer or wax.

4. The device of claim 1 comprising a patch.

5. The device of claim 1 wherein the membrane has a symmetric pore size throughout.

6. The device of claim 1 wherein the membrane has an asymmetric pore size throughout.

7. The device of claim 1 comprising biocompatible or biodegradable materials.

8. The device of claim 1 wherein the pharmaceutical is at a supersaturation concentration with additional solute present as suspended particles.

9. An aqueous-organic partitioning-based, diffusion-limited reservoir-containing controlled release pharmaceutical composition comprising a biodegradable or biocompatible microporous membrane comprising a hollow fiber having sealed ends or a film attached to a flat-ended reservoir and having pores extending through the microporous wall which are 1 nm to 10 $\mu$m in size and are filled with water and the fiber lumen or reservoir filled with a selected drug in a non-toxic organic solvent so that the selected drug in the fiber lumen or reservoir partitions into the water in the pores and diffuses through the water in the pores and out of the microporous membrane.

10. An aqueous-organic partitioning-based, diffusion-limited reservoir-containing controlled release pharmaceutical composition comprising a biodegradable or biocompatible microporous membrane comprising a hollow fiber having sealed ends or a film attached to a flat-ended reservoir and having pores extending through the microporous membrane wall which are 1 nm to 10 $\mu$m in size and are filled with a non-toxic organic solvent and the fiber lumen or reservoir filled with a selected drug in water so that the selected drug in the fiber lumen or reservoir partitions into the non-toxic organic solvent in the pores and diffuses through the non-toxic organic solvent in the pores and out of the microporous membrane.

* * * * *